United States Patent [19]

Richardson et al.

[11] Patent Number: 4,966,746

[45] Date of Patent: Oct. 30, 1990

[54] ULTRASONIC EXAMINATION OF BWR SHROUD ACCESS COVER PLATE RETAINING WELDS

[75] Inventors: David L. Richardson, Los Gatos; Jack P. Clark; Balasubramanian S. Kowdley, both of San Jose; Peter M. Patterson, Livermore; Richard W. Perry; Thurman D. Smith, both of San Jose, all of Calif.

[73] Assignee: General Electric Company, San Jose, Calif.

[21] Appl. No.: 293,158

[22] Filed: Jan. 3, 1989

[51] Int. Cl.⁵ .............................................. G21C 17/00
[52] U.S. Cl. .................................................... 376/249
[58] Field of Search ............... 376/249, 252, 245, 260; 73/621

[56] References Cited

U.S. PATENT DOCUMENTS

| | | | |
|---|---|---|---|
| 4,117,733 | 10/1978 | Gugel | 376/249 |
| 4,169,758 | 10/1979 | Blackstone et al. | 376/249 |
| 4,290,309 | 9/1981 | Charlebois et al. | 73/621 |
| 4,474,064 | 10/1984 | Naruse et al. | 376/249 |
| 4,642,215 | 2/1987 | Klinvex et al. | 376/249 |
| 4,826,650 | 5/1989 | Richardson et al. | 376/249 |

Primary Examiner—Daniel D. Wasil
Attorney, Agent, or Firm—Robert R. Schroeder

[57] ABSTRACT

In operation, the device is lowered with paired lines attached to both housing lugs but suspended under tension only from one line to one lug so that the streamline housing is vertically disposed. With the housing vertically disposed during lowering, obstacles can be avoided such as the guide rod for the steam separator and dryer as well as the feedwater and core spray spargers. When lowered to the vicinity of the ledge and cover plate to be inspected, the slack line is fished around any obstacle and thereafter placed under tension. The streamline housing is then lowered using both lines in a horizontal position so as to expose downwardly the pedestal and rubber foot. Lowering is completed with remote camera assistance. Sample sweeps with the ultrasound transducer of spaced apart sections of the cover plate weld are used for precise centering of the pedestal and rubber base with respect to the center of the cover plate. Repeatedly logging a longitudinal excursion of the ultrasound detector with indexed rotation of the housing permits scanning entirely around the weld of the cover plate. This enables remote ultrasound survey of the weld of the cover plate for stress corrosion cracking.

6 Claims, 4 Drawing Sheets

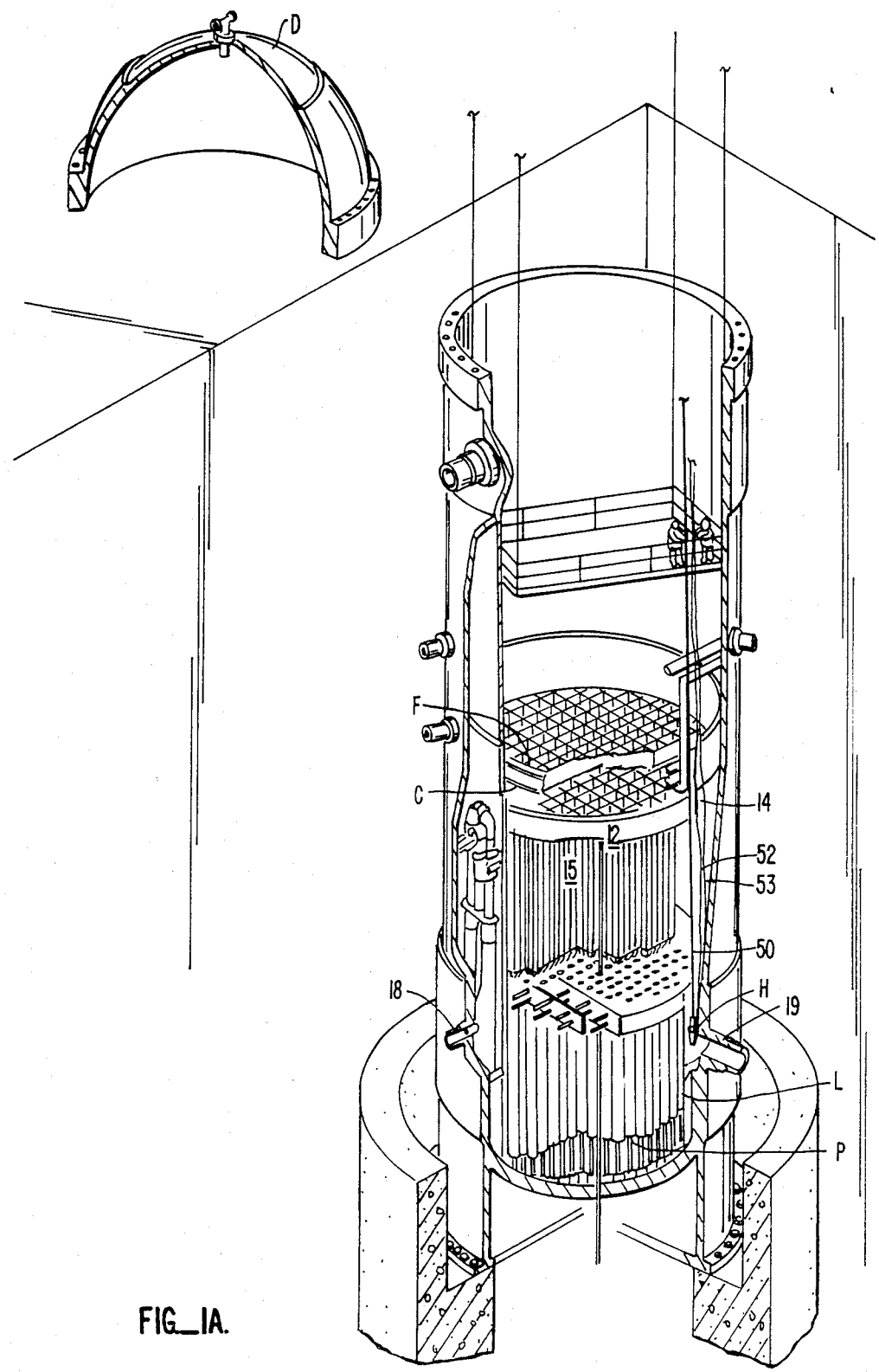
FIG_1A.

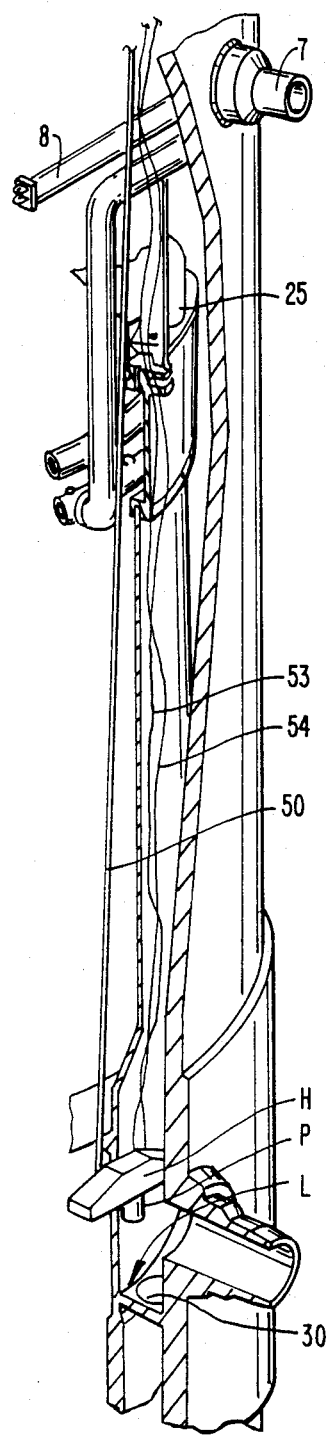
FIG._1B.
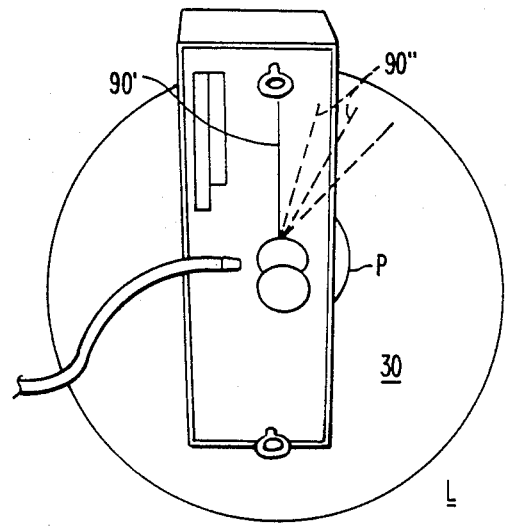
FIG._4.
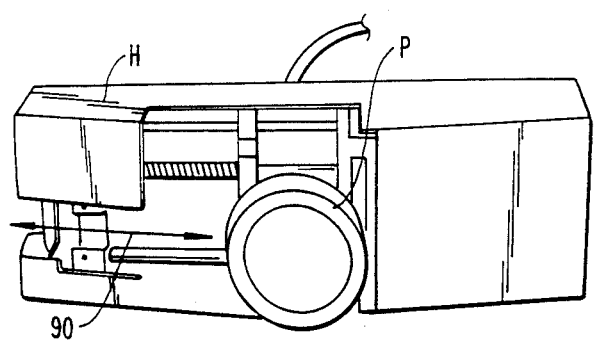
FIG._3.

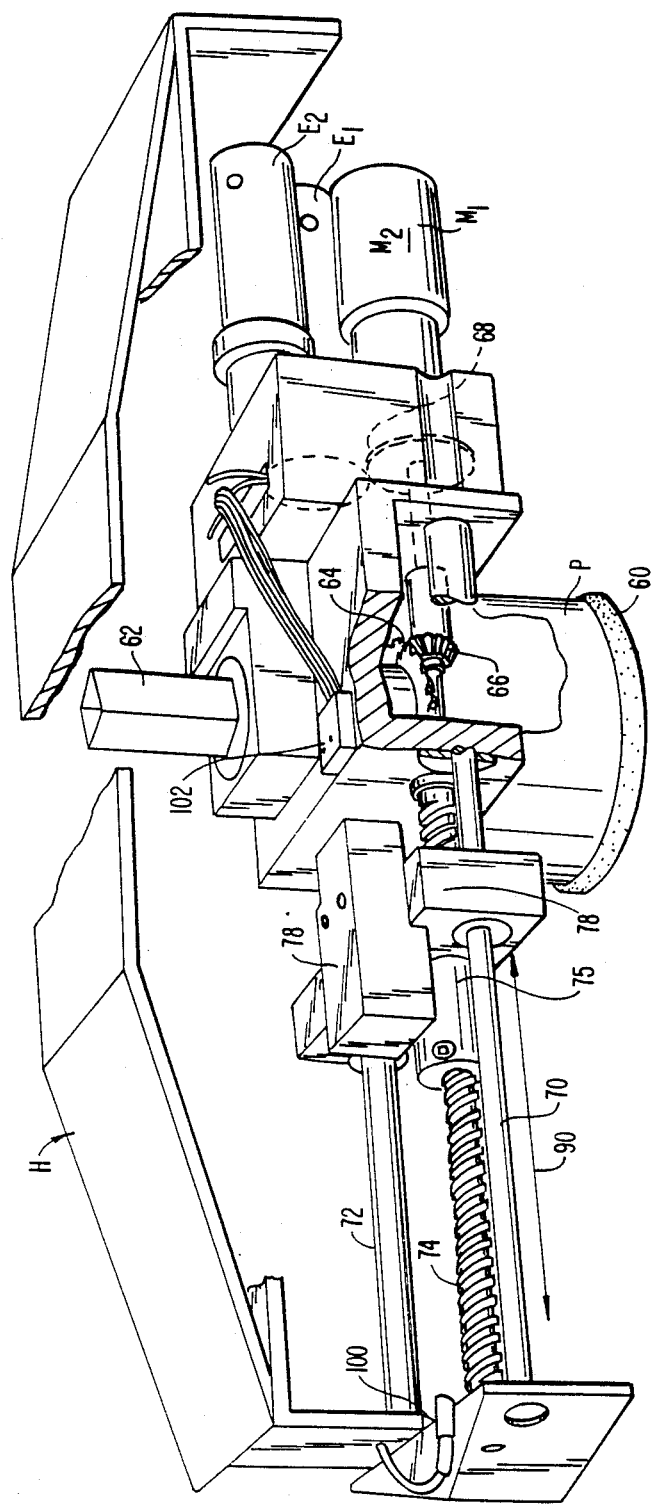
FIG._2.

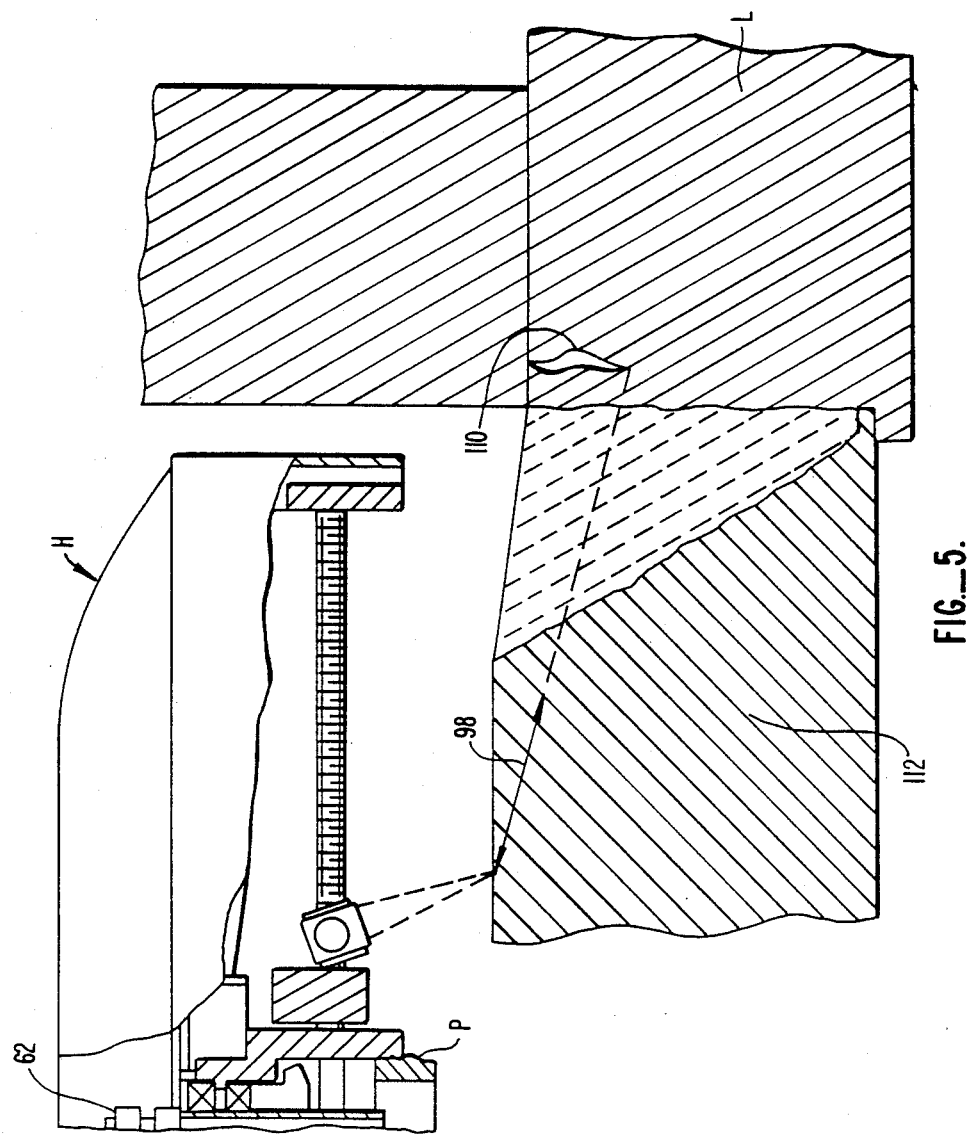
FIG._5.

ULTRASONIC EXAMINATION OF BWR SHROUD ACCESS COVER PLATE RETAINING WELDS

BACKGROUND OF THE INVENTION

This invention relates to the ultrasonic examination of a nuclear reactor boiling reactor. More particularly, an apparatus specialized for lowering to and the ultrasound inspection of an access cover plate at the plate retaining weld is disclosed. Heat effected portions of the weld and of the metal adjacent the weld are examined for stress corrosion cracking by a remote and automated ultrasound examination technique utilizing the disclosed apparatus.

BACKGROUND OF THE INVENTION

Boiling water nuclear reactors include access hatches which are required to be used in their construction. An example of such a required access hatch used in the construction of a reactor is the access to the coolant plenum below the reactor core. This plenum is in the bottom and most remote portion of a boiling water reactor.

The access to the plenum is open during reactor construction only. This access to the plenum occurs from the exterior of the reactor vessel, through the recirculating water outlet and down through an access hatch in the annular ledge forming the top of the plenum below the reactor core.

The access hatch during construction is utilized to permit the interior fabrication of the reactor elements within the plenum. These reactor elements within the plenum include the control rod guide tubes for the housing of withdrawn control rods and control rod drives. These same control rod guide tubes form the structural support of the weight of the overlying fuel bundles in the reactor core.

Once reactor construction is completed, the access is sealed by welding, the reactor permanently flooded and operation commenced.

In the BWR 6 reactors manufactured by the General Electric Company of Schenectady, N.Y., forced circulation of the water coolant interior of the reactor is utilized. This forced circulation uses a peripheral and annular downcoming region about the core to take water coolant and feedwater from the top of the core, force the flow of the coolant and feedwater down a peripheral annulus between a reactor core shroud on the inside and the reactor vessel sidewalls on the outside. From this defined annulus, the water flows by pumping into the plenum containing the control rod guide tubes below the core.

Jet pumps for pumping the water within the annulus between the core shroud and the vessel walls are used for the required pumping. These jet pumps intake at the top of the annulus, force the circulation downwardly, and discharge through apertures in the peripheral downcoming region. Thus, the plenum below the core becomes a relatively high pressure region in comparison to the remainder of the reactor. Consequently, water flow is induced upwardly through the core by passage through the control rod guide tubes, the fuel bundles support castings, and then through the fuel bundles and bypass region of the core.

The jet pumps in the annular region between the sides of the core and the inside of the vessel wall require a supply of high pressure, low volume water for their powering jets. Typically, such jets have a coolant inlet for receiving the water to be pumped, a mixing section into which the pump powering jet of water is introduced, and a diffuser section which effectively transfers the momentum of the low volume, high pressure pumping jet to a high volume, low pressure flow of intermixed pumping water and entrained water exiting the mixer of the pump. There results the high volume, low pressure flow into the lower plenum sufficient to cause the forced circulation upwardly through the core.

The jet pumps are powered by exterior recirculation pumps. The suction or supply for the recirculation pumps is taken from the peripheral annulus through the vessel sidewalls. This peripheral annulus is closed at the bottom by a peripheral annular ledge. This peripheral annular ledge forms the boundary between the lower plenum below and the down coming annulus above.

Two recirculation water outlets pass through the reactor vessel sidewall on opposite sides of the reactor vessel. They draw suction from the down coming annulus. Water for powering the jet pumps is drawn through the recirculation water outlet to the recirculation pumps, passed through the pumps, and then reentered through the reactor vessel sidewalls to the jet section of the jet pumps.

During the operation of the reactor, the peripheral, annular ledge constitutes a pressure barrier. On the lower side of the peripheral annular ledge is the plenum, the plenum being the high pressure portion of the reactor for the forcing of circulation upwardly through the core. On the upper side of the peripheral annular ledge and within the upwardly exposed annulus is the extreme low pressure region. This is the region where suction is taken to the forced circulation inducing pumps.

It has been found that the welded cover plate at the access hatch is a candidate for stress corrosion cracking. Metal under heat induced stress within and adjacent the weld is present. The water coolant of the reactor provides the required chemistry for stress corrosion cracking with small amounts of entrained oxygen. Given normal aging, the welds of the access cover plate and the metal adjacent the welds have exhibited in certain reactors stress corrosion cracking.

From the foregoing description, the reader can understand.

Inspection of the weld at the access hatch cover during outages is desirable.

Second, access for inspection is other than convenient. Accordingly, this disclosure is a solution to this problem.

SUMMARY OF THE INVENTION

An apparatus and process for the remote inspection for stress corrosion cracking of welded shut boiling water reactor shroud access cover plates is disclosed. The apparatus consists of a streamline housing having a top side with lugs for the attachment of lowering lines on either end of the housing. Medially of the streamline housing and projecting downwardly from the bottom of the streamline housing, there is provided a central and stationary pedestal with a rubber base. The stationary pedestal and rubber base enable the entire housing to rest on and rotate relative to the pedestal and rubber base. A first motor interior of the housing rotates the housing at a bevel gear rigidly mounted to the central pedestal. A second motor rotates a threaded shaft driving a ball screw with an attached mount for an ultrasound transducer. The mount and transducer responsive to rotation of the ball screw traverse along the elongate dimension of the housing over an opening through the bottom of the housing. A focused ultrasound transducer passes above the metal to be inspected. This ultrasound transducer focuses the sound through the water at an oblique angle to and from the metal of the hatch cover plate for an ultrasonic examination for stress corrosion cracking. In operation, the device is lowered with paired lines attached to both lugs but suspended under tension only from one line to one lug so that the streamline housing is vertically disposed. With the housing vertically disposed during lowering, obstacles can be avoided such as the guide rod for the steam separator and dryer as well as the feedwater and core spray spargers. When lowered to the vicinity of the ledge and cover plate to be inspected, the slack line is fished around any obstacle and thereafter placed under tension. The streamline housing is then lowered using both lines in a horizontal position so as to expose downwardly the pedestal and rubber foot. Lowering is completed with remote camera assistance onto the hatch to be inspected. The central pedestal is typically located centrally of the hatch. Sample sweeps with the ultrasound transducer of spaced apart sections of the cover plate weld are used for precise centering of the pedestal and rubber base with respect to the center of the cover plate. Upon completion of the required centering, logging longitudinal excursion of the ultrasound detector with following indexed rotation of the housing entirely around the weld of the cover plate to be surveyed occurs. This enables remote ultrasound survey of the weld of the cover plate for stress corrosion cracking.

Other Objects, Features and Advantages

An object to this invention is to disclose a simple device for the automated scanning in a submersed environment. Accordingly, a streamline longitudinal housing is utilized. The housing contains at the top portion thereof paired, spaced apart line attachment points for the lowering of the housing by one or the other or both lines. Protruding medially from the housing at the bottom thereof is a base. The base has a rubber mount for resting upon the hatch cover to be examined. There is provided a first motor for effecting rotation of the housing with respect to the base. There is provided a second motor driving a ball screw and sound transducer mount longitudinally of the housing. The sound transducer is focused downwardly and obliquely with respect to its path through an opening in the bottom of the housing. At either end of the sound transducer mount there are provided limits switches for reversing the direction of scan. These limits switches are operatively connected to rotate the mount on the pedestal typically by effecting incremental rotation at the end of each longitudinal pass of the ultrasound transducer.

An advantage of the disclosed apparatus is that once it is centered with respect to a welded cover plate to be surveyed, the survey may proceed in an automated fashion. Specifically, with each longitudinal excursion of the sound transducer on the housing, rotational indexing of the housing by selected incremental amounts over the circumference of the cover plate weld occurs.

Yet another object to this invention is to set forth a process of utilizing the disclosed ultrasound transducer housing in the submerged environment within the remote region overlying the lower plenum of the reactor. According to this aspect of the invention, the housing is lowered by one line so that the housing disposes itself into a vertically aligned disposition. In such a vertically aligned disposition, the streamline housing avoids entanglement with components interior of the reactor such as the guide rod (for aligning the dryer and steam separator) and the feedwater and core spray spargers.

When the streamlined housing is lowered in the vertical disposition below all obstacles, the slack line is fished around the obstacles. Once fished around all obstacles, the housing is lowered thereafter using two lines so as to impart to the housing a two point support. The housing is manipulated to a horizontal position with the pedestal depending to and towards the bottom. Thereafter, and with remote camera assist, the device is centered with respect to a hatch.

An advantage of this aspect of the invention is that the disclosed apparatus can be threaded through obstacles to the remote location to be examined. At the same time, and upon arrival at the cover to be inspected, the device can be horizontally disposed for the required automated ultrasound inspection.

BRIEF DESCRIPTION OF THE DRAWINGS

Other objects, features and advantages of this invention will become more apparent after referring to the attached specification and drawings in which:

FIG 1A is a view of a reactor vessel with the steam dome, steam dryer and steam separator removed during an outage and illustrating maintenance personnel lowering the apparatus of this invention to and between of the shroud core surrounding and the vessel sides;

FIG. 1B is an enlargement of the reactor at the shroud illustrating the annular ledge on which the access hatch has been welded shut by the cover plate showing the apparatus of this invention being lowered in a horizontal disposition to the access cover plate to be inspected;

FIG. 2 is an operable schematic of the disclosed apparatus for cover plate inspection illustrating the longitudinal housing without its streamlined cover, the pedestal on which the housing turns and the reciprocating mount to which the ultrasound transducer is attached;

FIG. 3 is a view of the apparatus of FIG. 2 from the bottom illustrating the downwardly exposed rubber foot at the bottom of the pedestal and the path along which the sound transducer passes for the ultrasound inspection;

FIG. 4 is a schematic illustration showing the apparatus on a cover plate with a typical path of the transducer indicated in broken lines; and FIG. 5 is a cross-section taken at a cover plate illustrating the oblique incidence of focused sound from the ultrasound transducer inspecting a weld and illustrating the theoretical detection of stress corrosion cracking in the metal of and adjacent to the weld being inspected.

Referring to FIG. 1A, a reactor vessel V is illustrated having its steam dome D removed. Its steam dryer Y has been removed and its steam separator assembly S has likewise been removed. The dryer and separator are disposed in a holding pool adjacent the reactor.

Maintenance personnel M are shown lowering a housing H. The housing H is shown vertically disposed by one line under tension. The housing H is passing the feedwater sparger F and the core spray sparger C in the vertical position. The housing H is thus on its way being lowered to an annular ledge L defining the bottom of the upwardly exposed annulus defined by the core shroud 14.

By way of summary, water is circulated interior of the reactor from a lower plenum P, upwardly through core 15. Steam formed in the reactor core passes through the steam separator S and the dryer Y, and then outwardly to turbine equipment.

Coolant not generated into steam passes over the top guide 12, downwardly into the upwardly exposed annulus defined by the core shroud 14. At annulus 14, jet pumps 13 pump the coolant downwardly to the plenum P where the recirculation cycle interior of the vessel V endlessly repeats.

Powering of the jet pumps can be easily understood. Typically, a recirculating water outlet 19 passes water to low volume, high pressure pumps (not shown). Water returning from the pumps is inlet through inlet 18 where it powers jet pumps 13. Jet pumps 13 draw fluid along the upwardly disposed annulus defined by core shroud 14 and pass it through diffuser outlet holes in ledge L. Thus, forced circulation is induced along the side of core shroud 14.

Turning to FIG. 1B, the particular access hatch to be inspected can be seen to be at an extremely inconvenient portion of the reactor for access.

Remembering that the reactor is normally flooded, the access problem encountered by this invention can be best understood by referring to FIG. 1B.

Feedwater is inlet through aperture 7 and outlet at a feedwater sparger 8. This apparatus constitutes an obstacle.

An emergency core spray sparger 11 is shown for maintaining water on the reactor core during certain emergencies. This constitutes and additional obstacle.

Finally, there is a guide rod 25. Guide rod 25 is utilized to accurately position both the steam separator S and the dryer Y. It will be understood that the feedwater sparger 8, the core spray sparger 11, and the guide rod 25 all constitute obstacles which the housing H must pass in transit to the site of the desired ultrasound inspection.

Consequently, and as illustrated in FIG. 1, the housing H is lowered with its elongate dimension vertically disposed to thread around these obstacles. It is typically lowered by a single line 50 with a slack line 52 and its control cable 53 not taught.

Referring to FIG. 1B, housing H is shown horizontally disposed. This horizontal disposition is made possible by support of the housing at both lines 50 and 52. As before, control table 53 is essentially slack.

It will be understood that before the housing was supported in the horizontal position, that line 52 has been fished around obstacles encountered in lowering. After such fishing, line 52 is pulled taut and in the horizontal both lines 50, 52 are used for the required lowering.

It can be seen in FIG. 1B that pedestal P is being lowered towards cover plate 30. Assisting television monitors with illuminating lights are conventional and therefore not shown.

Having set forth the manner in which the apparatus of this invention gains access to the interior ledge L, its construction can now be set forth.

Referring to FIG. 2, housing H includes a pedestal P with a lower rubber foot 60. A bearing 62 attaches to the pedestal P. This bearing has attached a bevel gear 64. A motor M1 rotates a meshing bevel gear 66. A shaft encoder meshed by gears 68 measures the rotation of motor M1 and through applicable control cables indicates total rotation of motor M1 and consequently the rotation of the housing on the pedestal P.

It can thus be understood that housing H can rotate on pedestal P.

Interiorly thereof, housing H includes first and second slider shafts 70 and 72. Mounted between slider shafts 70 and 72 is a screw 74. A ball screw follower 75 follows rotation of the shaft 74 and moves a transducer mount 78 on slider shafts 70, 72. Rotation of the ball screw is easily understood.

Typically, motor M2 effects rotation of the threaded shaft 74. Transducer mount 78 traverses the ball screw. Thus, scanning longitudinally of the housing occurs through movement of an ultrasound transducer T on mount 78.

Referring to FIG. 3, the housing is shown with a bottom plan view. Pedestal P and housing H are illustrated. It can be seen that the transducer at the bottom of the housing has a linear scan path 90.

Returning briefly to FIG. 2, a first limit switch 100 at one end of mount excursion and a second limit switch 102 at the other end of mount excursion are shown. These limit switches are contacted by transducer mount at either end of the excursion path 90 followed by the transducer mount. Upon contact with the limit switch, motor M2 reverses. Alternately, such motor reversal can occur responsive to counts from the shaft encoder.

Referring to FIG. 4, an exaggerated view of the path followed by the transducer can be seen.

Specifically, the cover plate 30 is shown in the ledge L. It can be seen that the pedestal P rests upon the approximate center of the cover plate 30. The transducer makes a first linear pass 90'. At the end of the linear pass, a limit switch 100 or 102 is contacted. Upon contact of the limit switch, housing H rotates incrementally in the clockwise direction by a small amount. Typically, this small amount is measured in fractions f an inch at the circumference of the weld. Upon the end of this rotation, the transducer makes a second linear scan along path 90''. Naturally, the process is repeated until the entire cover has been ultrasonically scanned for inspection.

Referring to FIG. 5, a typical path of the acoustical inspection interior of the weld is illustrated. Housing H is shown overlying and resting on cover 112. Such resting occurs at the pedestal, which pedestal is not shown in this view.

An ultrasound transducer T shown on a mount M passes a focused ultrasound beam 98 through the water interior of the reactor to the top surface of the cover 112 to be inspected.

Focused beam 98 undergoes deflection induced by the metal water interface in the metal of cover plate 112. This is shown in the acute and increased angle of incidence at path 98 in the metal.

The incident path and the reflected path will both be approximately the same and therefore within path 98. Defects, such as stress corrosion cracking 110, will be evident in the timing of the return signal as is conventional. Consequently, the timing of the return signals leading to a logged signal of the cover cracking profile will not further be discussed except to mention that one normal local for such cracking is adjacent the weld 105 in the metal of the annular ledge L.

It will be understood that the cover plate is supported on a ledge 104. It is this ledge that forms a usual support point where detachment of the plate from the ledge L occurs.

The reader will understand that the configuration of the cover 112 will vary from reactor to reactor in accordance with the original constructed design. However, the general principles enumerated herein are believed sufficient for inspection of all varieties of covers known.

We claim:

1. A process for the inspection of a welded shut hatch cover plate at the peripheral ledge forming the boundary between the plenum below the flooded core of a boiling water nuclear reactor and the upwardly exposed and flooded shroud annulus for recirculating the water for reactor forced circulation, the inspection process occurring in a boiling water nuclear reactor during an outage when the reactor steam dome, steam dryer, and steam separator are removed for direct access to the interior of the flooded reactor, the process comprising the steps of:

providing a submersible housing having a top side with at least one attachment point and a lower rotative pedestal for the resting support of the housing on said pedestal;

providing a first motor mounted to said submersible housing operatively connected to said pedestal for causing said housing to rotate relative to said pedestal;

providing an ultrasound transducer mounted on a longitudinally sliding mount, said ultrasound transducer focused downwardly from an opening in the bottom of said submerged housing, said ultrasound transducer connected for longitudinal logging excursion of metal immediately underlying said housing when said housing rests at said pedestal on said metal;

providing a second motor mounted to said submersible housing said motor operatively connected to said sliding mount for causing longitudinal excursion of said ultrasound mount for ultrasonic inspection of welds under said housing;

lowering said submersible housing from a support point in the top of said housing in the defined shroud annulus between the flooded reactor vessel core and reactor vessel sidewall into the bottom ledge of said upwardly exposed shroud annulus;

placing the pedestal of said housing on the center of said cover plate to be inspected at the end of said lowering steps;

driving said first and second motors for combined longitudinal excursion of said ultrasound transducer and incremental rotation of said housing on said pedestal for logged ultrasound inspection of said cover plate, weld and peripheral ledge adjacent said cover plate.

2. The process of claim 1 and wherein first and second lines are used for the lowering of said housing.

3. The process of claim 2 and wherein the lowering of said housing occurs with said housing vertically disposed.

4. The process of claim 1 and including the step of operably connecting said motors and sound transducer through conduits to the surface of said reactor for control.

5. The process of claim 1 and wherein said provided ultrasound transducer focuses sound through water into the metal of said cover plate to be inspected.

6. The process of claim 5 and wherein said sound is angularly incident on said metal for the inspection of welds.

* * * * *